(12) United States Patent
Lee et al.

(10) Patent No.: US 11,655,507 B2
(45) Date of Patent: May 23, 2023

(54) METHOD FOR DIAGNOSING PARKINSON'S DISEASE USING NASAL MUCUS, COMPOSITION THEREFORE, AND KIT COMPRISING THE SAME

(71) Applicants: Research & Business Foundation Sungkyunkwan University, Suwon-si (KR); IUCF-HYU (Industry-University Cooperation Foundation Hanyang University), Seoul (KR)

(72) Inventors: Yunjong Lee, Cheongju-si (KR); Hyojung Kim, Daegu (KR); Seok-Hyun Cho, Seoul (KR); Seok-Jae Kang, Gwacheon-si (KR); Hee-Tae Kim, Seoul (KR)

(73) Assignees: Research & Business Foundation Sungkyunkwan University, Suwon-si (KR); IUCF-HYU (Industry-University Cooperation Foundation Hanyang University), Seoul (KR)

( * ) Notice: Subject to any disclaimer, the term of this patent is extended or adjusted under 35 U.S.C. 154(b) by 756 days.

(21) Appl. No.: 16/568,743

(22) Filed: Sep. 12, 2019

(65) Prior Publication Data
US 2021/0079469 A1    Mar. 18, 2021

(51) Int. Cl.
*C12Q 1/6883* (2018.01)
*C12Q 1/6851* (2018.01)

(52) U.S. Cl.
CPC ......... *C12Q 1/6883* (2013.01); *C12Q 1/6851* (2013.01); *C12Q 2545/101* (2013.01); *C12Q 2600/112* (2013.01); *C12Q 2600/118* (2013.01); *C12Q 2600/158* (2013.01); *C12Q 2600/166* (2013.01)

(58) Field of Classification Search
None
See application file for complete search history.

(56) References Cited

U.S. PATENT DOCUMENTS

2012/0122958 A1 *    5/2012   Dawson ......... C12Y 603/02019
                                              435/7.1

OTHER PUBLICATIONS

Benson et al Clin Exp Allergy. 2005. 356:473-478 (Year: 2005).*
Watts et al. Int Arch Allergy Immunol. Jun. 2018. 177: 29-34 (Year: 2017).*
Lee et al Otolaryngology—Head and Neck Surgery. 2009. 140: 197-201 (Year: 2009).*
Jonsson et al Int Arch Occup Environ Health. 2009. 82: 1261-1266 (Year: 2009).*
Kim, Hyojung et al., "Quantitative analysis of nasal transcripts reveals potential biomarkers for Parkinson's disease", Scientific Reports, Jul. 31, 2019 (pp. 1-9).

* cited by examiner

*Primary Examiner* — Carla J Myers
(74) *Attorney, Agent, or Firm* — NSIP Law

(57) ABSTRACT

The present disclosure relates to a method for diagnosing Parkinson's disease in which the method includes measuring the expression level of Parkinson's disease-related genes from a subject's nasal mucus sample, a composition for diagnosing Parkinson's disease, and a kit including the same.

12 Claims, 12 Drawing Sheets
Specification includes a Sequence Listing.

[Fig. 1A]
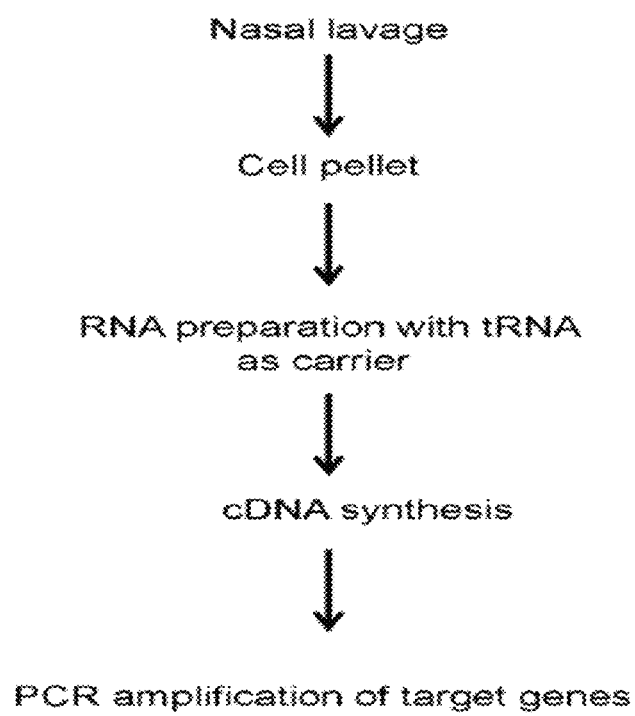

[Fig. 1B]
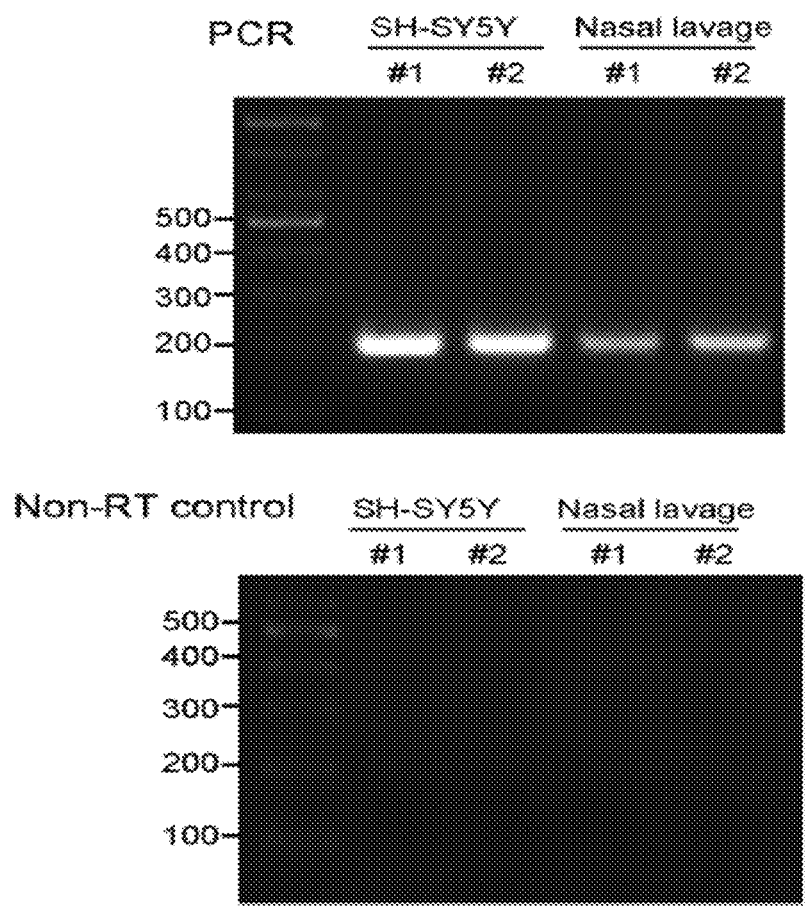

[Fig 2A]
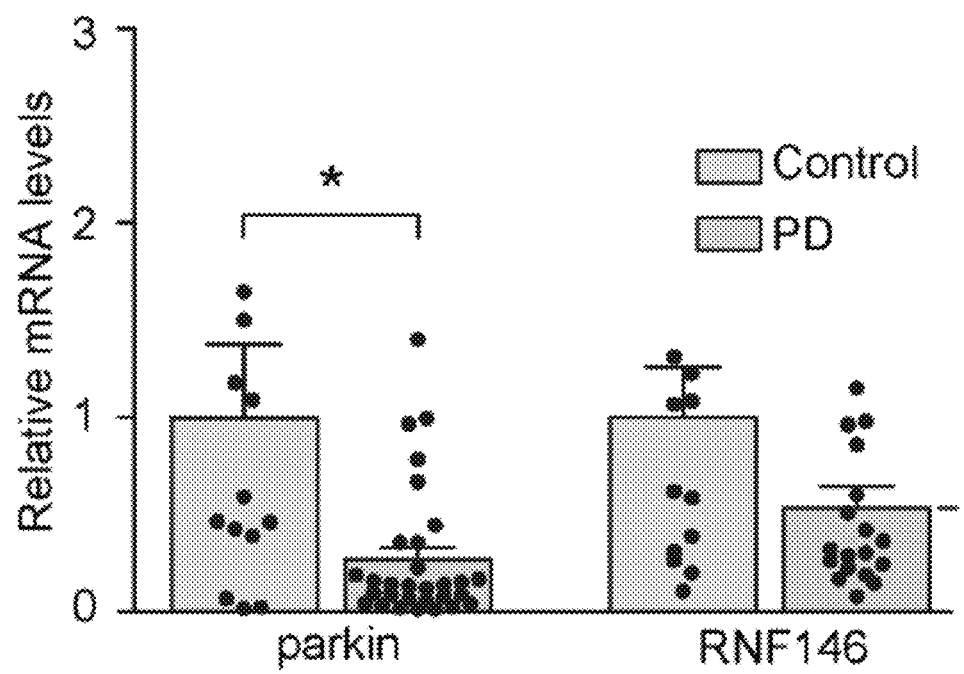

[Fig 2B]
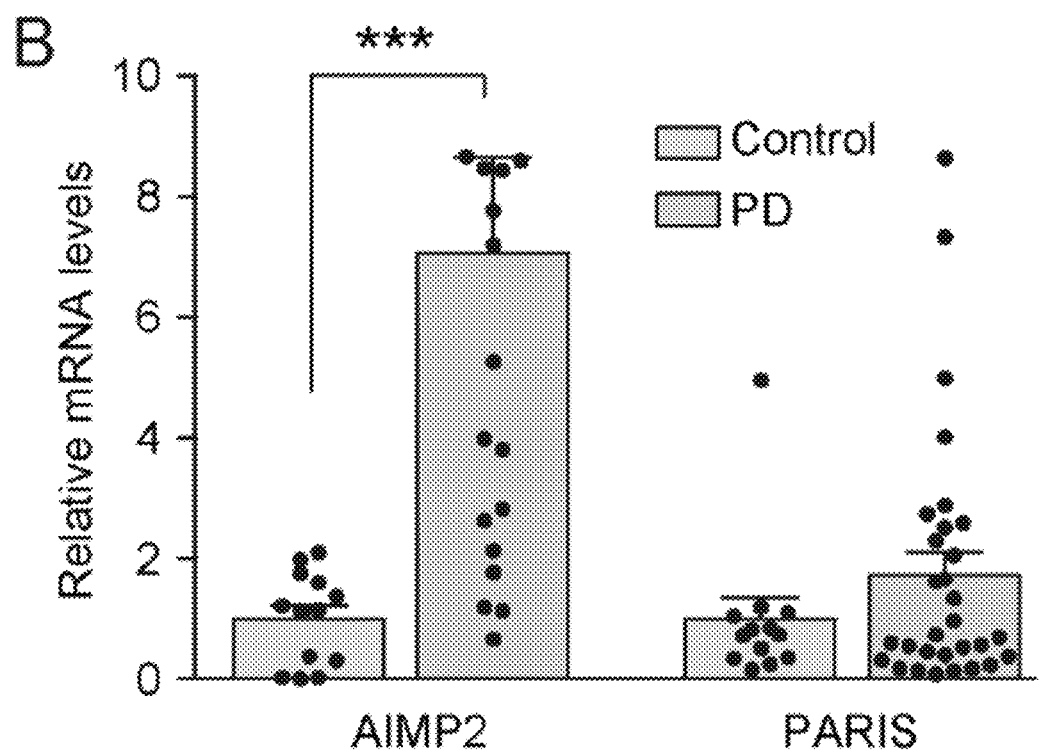

[Fig 2C]
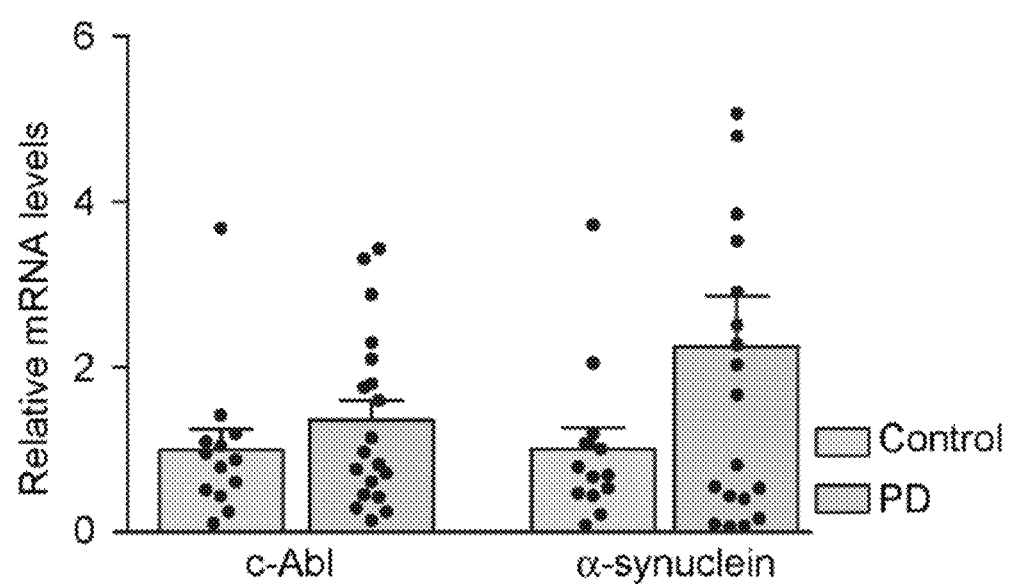

[Fig 3A]
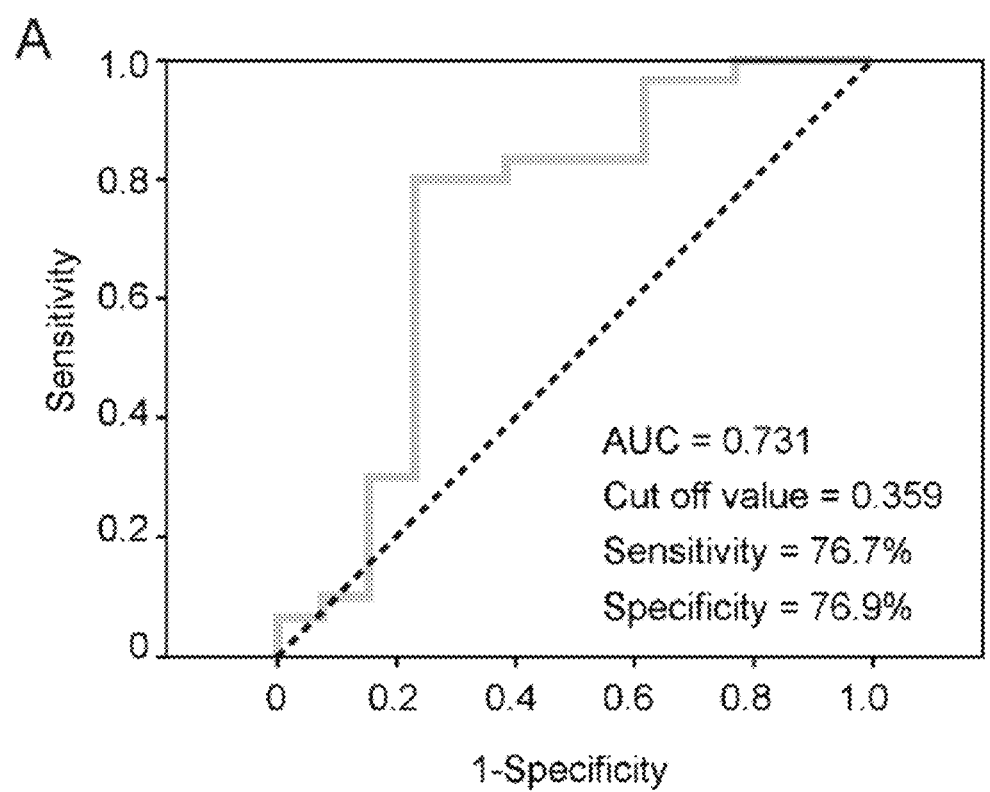

[Fig 3B]
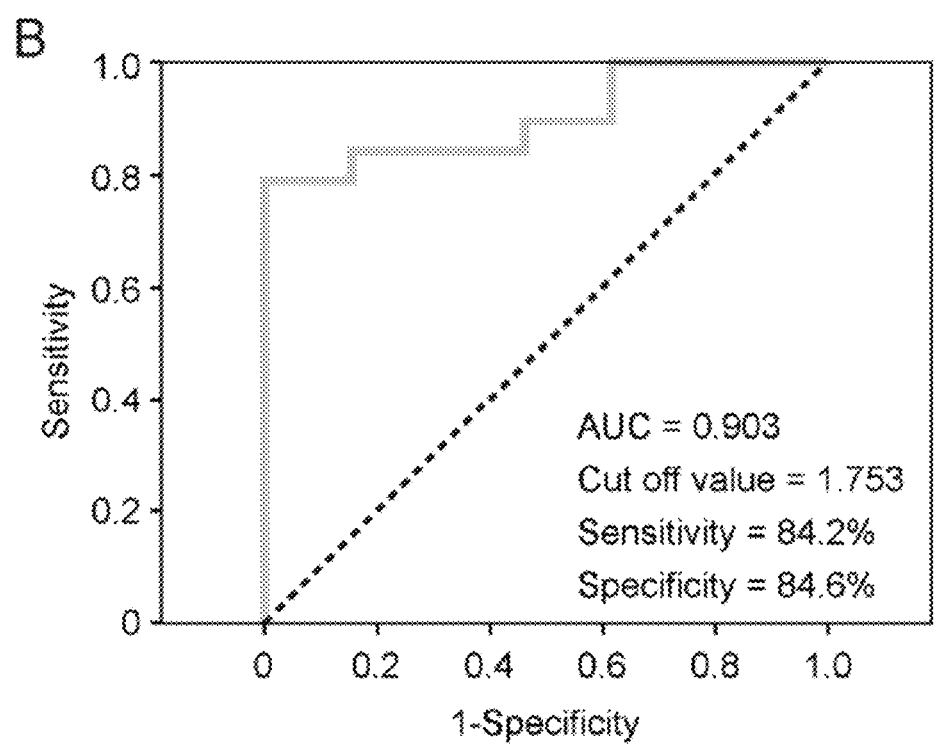

[Fig 4A]
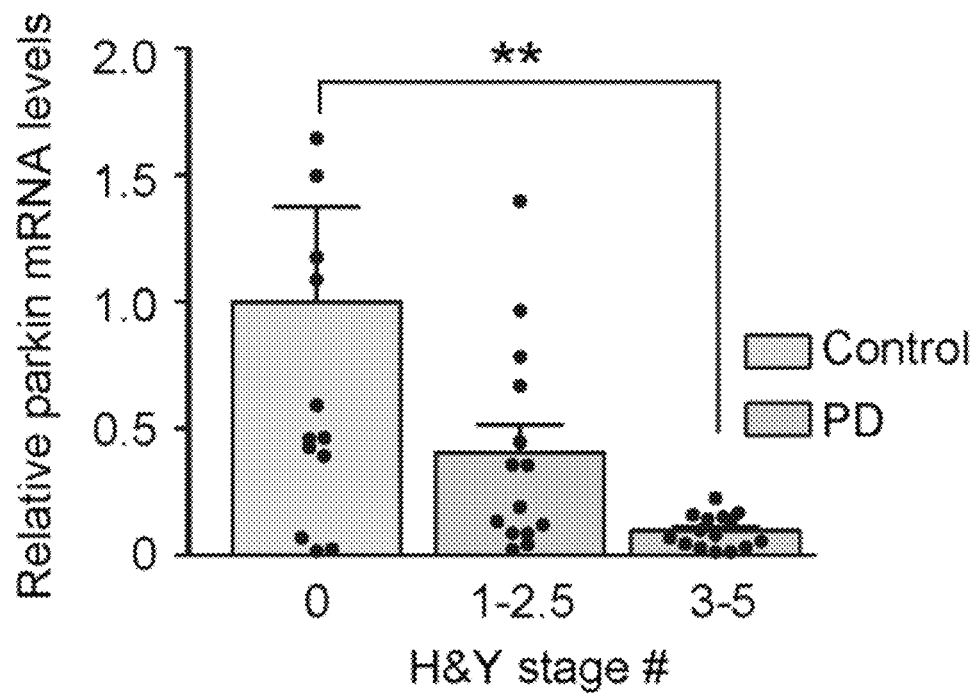

[Fig 4B]
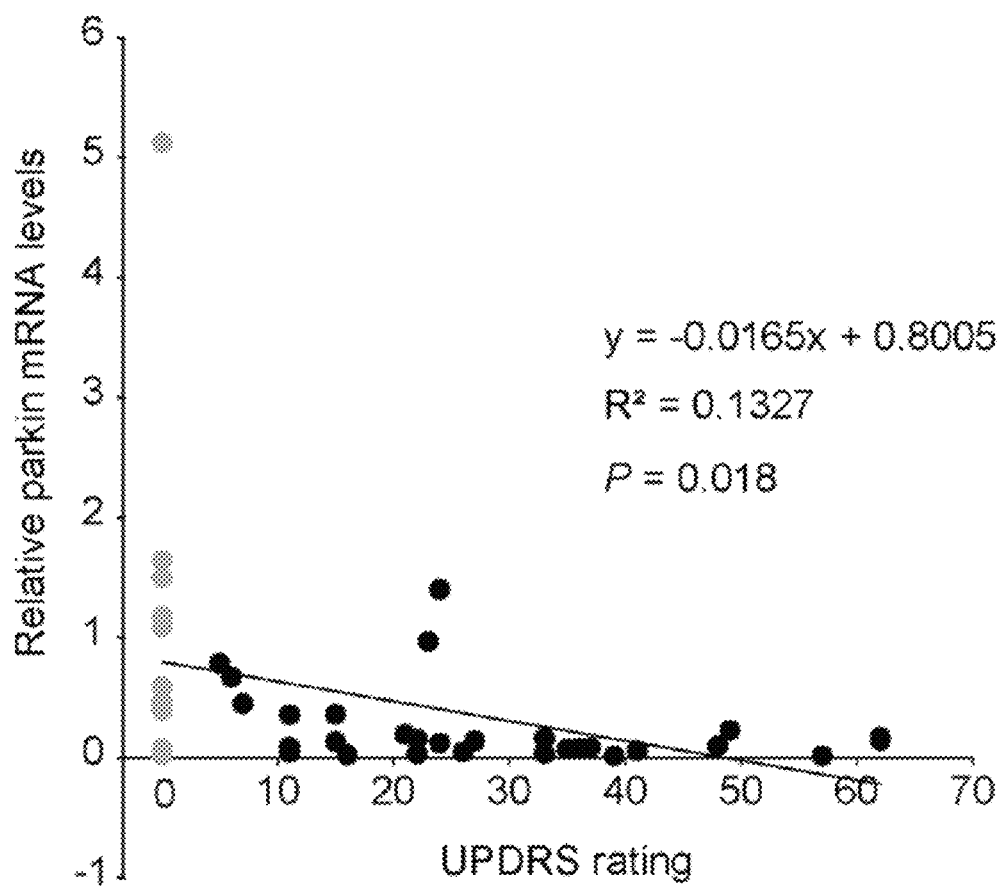

[Fig 4C]
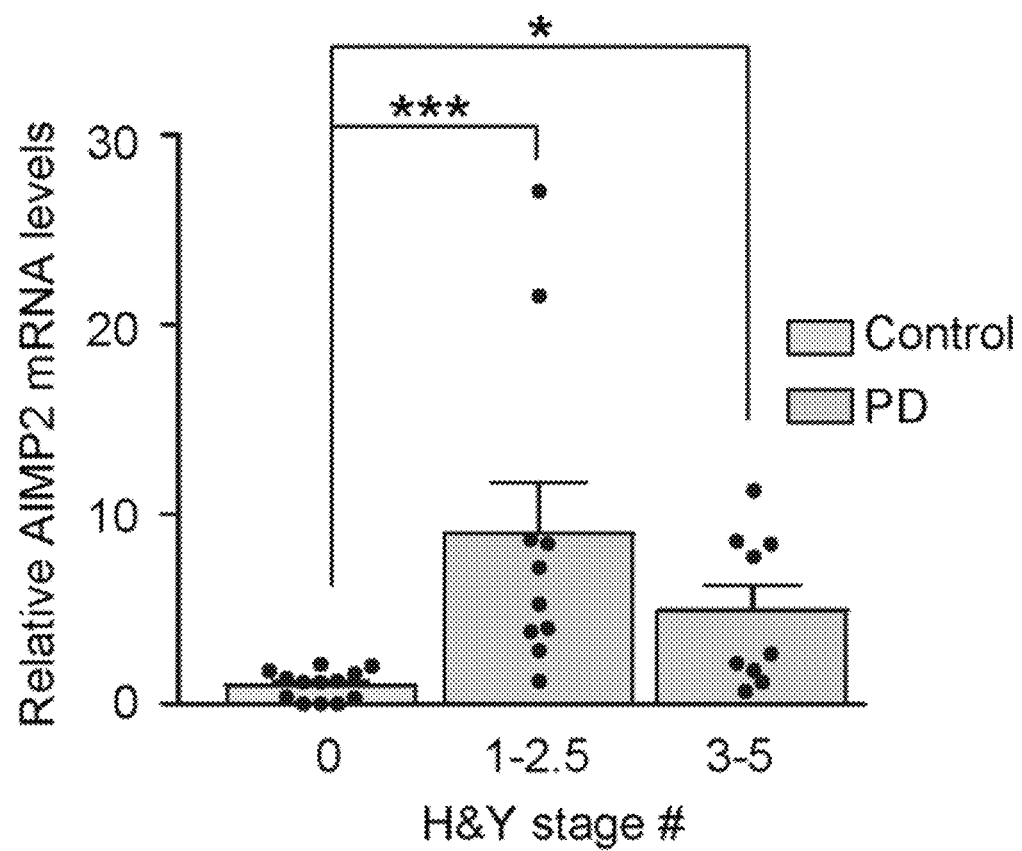

[Fig 4D]
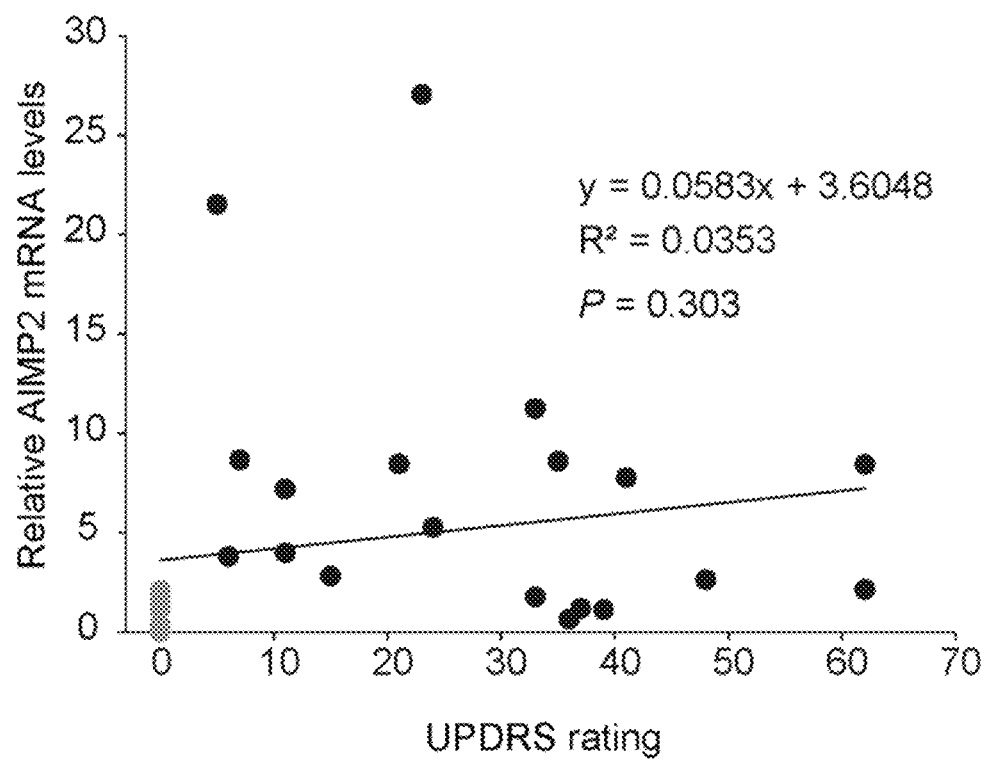

[Fig 5]
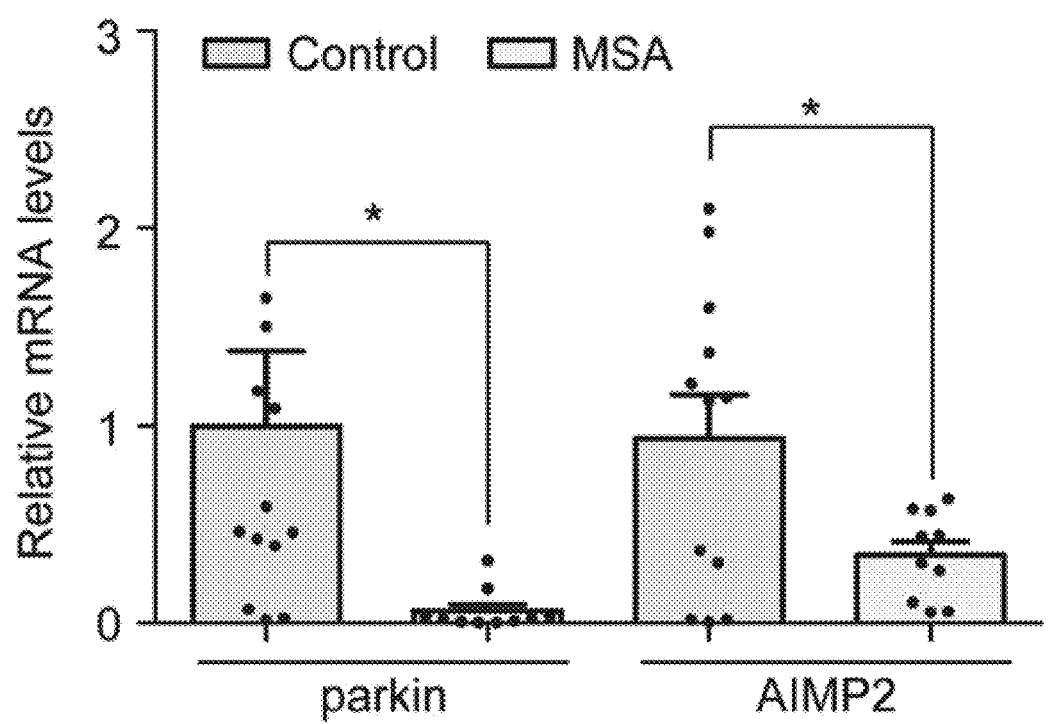

METHOD FOR DIAGNOSING PARKINSON'S DISEASE USING NASAL MUCUS, COMPOSITION THEREFORE, AND KIT COMPRISING THE SAME

TECHNICAL FIELD

The present disclosure relates to a method for diagnosing Parkinson's disease in which the method includes measuring the expression level of Parkinson's disease related genes from a subject's nasal mucus sample, a composition for diagnosing Parkinson's disease, and a kit including the same.

BACKGROUND

As life expectancy increases and societies age, degenerative diseases caused by aging are becoming a major medical and social problem. Of these degenerative diseases, in particular the number of patients with Parkinson's disease, degenerative dyskinesia, is dramatically increasing.

Parkinson's disease refers to a degenerative neurological disease in which the muscles of the arms, legs or whole body are convulsed or stiff resulting in no center and balance. This symptom is caused by a problem in the nerve cells and occurs when the secretion of dopamine, a neurotransmitter, is abnormal, and certain neurons in the brain are gradually destroyed. Typical symptoms of Parkinson's disease are dyskinesia, including convulsions, muscle stiffness and slow motion.

Since Parkinson's disease is slow to progress, and it progresses over decades, it is difficult to know exactly when it occurs. In many cases, when the symptoms were found, the nerve cells in the brain's black matter had already degenerated significantly. Therefore, in order to properly control Parkinson's disease lesion progression and to effectively treat and prevent lesions, it is important to discover new disease-specific markers that can be early diagnosed before significant neuronal cell death occurs.

Currently, cerebrospinal fluid, blood, and urine are used as biosecretory samples for early diagnosis of Parkinson's disease. However, cerebrospinal fluid is limited in the amount of sample which may be collected, and it is difficult to obtain a sample for research and diagnostic purposes so that there was a limit to analyzing various types of markers at the same time. Although blood and urine have an advantage because they may be collected in a non-invasive way compared to cerebrospinal fluid, there may be a problem in sensitivity or consistency because it is an indirect diagnostic marker measurement in a sample that does not directly represent the development site of lesion of degenerative disease. Thus, there is currently no clinically available biological sample, and it is considered to be a major obstacle in the early diagnosis and development of new drugs for Parkinson's disease.

PRIOR ART DOCUMENTS

Patent Document

Korea Patent No. 10-1716114

SUMMARY

The present disclosure noted that more than 80% of Parkinson's patients were reported early olfactory abnormalities, and developed a transcriptome analysis method using nasal mucus that is easy to collect samples as an early diagnosis strategy for Parkinson's disease. Parkinson's patients may have early olfactory abnormalities, and thus it is hypothesized that peripheral lesions may occur in advance of Parkinson's central lesions. To date, there has no been attempt to early diagnose Parkinson's disease using nasal mucus.

Accordingly, the present disclosure extracts and isolates transcript RNA from nasal mucus and is to quantify expression levels of major Parkinson's disease markers (α-synuclein (SNCA), parkin, ZNF746 (PARIS), RNF146, c-Abl and AIMP2) using real-time quantitative PCR technique from this. In addition, the present disclosure is to utilize the markers associated with Parkinson's lesions as early diagnostic markers of Parkinson's disease lesions from analysis of nasal mucus transcript of normal group and Parkinson's patients.

However, the issues to be addressed by the present disclosure are not limited to the above-mentioned issues, and other issues not mentioned are clearly understood by those skilled in the art from the following description.

The first aspect of the present disclosure may provide a composition for diagnosing Parkinson's disease, in which the composition includes an agent for measuring the expression level of Parkinson's disease-related gene from isolated nasal mucus.

The second aspect of the present disclosure may provide a kit for diagnosing Parkinson's disease in which the kit includes the composition for diagnosing Parkinson's disease according to the first aspect of the present disclosure.

The third aspect of the present disclosure may provide a method for diagnosing Parkinson's disease, in which the method includes: separating nasal mucus from a suspected patient of Parkinson's disease; measuring expression level of a Parkinson's disease-related gene transcript, or a peptide or a protein expressed therefrom, from the cells in the nasal mucus and normalizing the measured results to expression of standard genes; and comparing the normalized expression level with the normalized expression level measured for normal subjects.

The above-mentioned means for solving the problems are only exemplary, and should not be construed to limit the present disclosure. In addition to the exemplary embodiments described above, there may be additional embodiments and Example described in the drawings and detailed description of the disclosure.

The present disclosure is to provide a method for early diagnosis or confirmation of Parkinson's disease by quantifying Parkinson's disease markers which is specific to nasal mucus in nasal mucus transcripts of potential Parkinson's disease patients with olfactory abnormalities. In particular, the analysis of nasal mucus transcripts in normal and Parkinson's patients confirms that the decrease of Parkin's transcripts and the increase of AIMP2 transcripts are significantly associated with Parkinson's lesions. Thus, the present disclosure aims to utilize Parkin and AIMP2 in nasal mucus as early diagnostic markers of Parkinson's disease lesions. Further, the present disclosure aims to utilize the isolation and purification of transcripts from nasal mucus and the quantification of Parkin and AIMP2 transcripts for the development of efficient and selective sensitive diagnostic kits of Parkinson's disease.

The present disclosure is the first to quantify transcripts in nasal mucus in patients with Parkinson's disease and is to provide a method for early diagnosis of Parkinson's disease from the expression patterns of nasal mucus transcript-specific Parkinson's disease markers.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1A is a flowchart of a process for quantifying target gene transcripts from nasal mucus according to one embodiment of the present disclosure, and FIG. 1B is a view showing an electrophoresis result confirming that target gene transcripts are normally purified from nasal mucus.

FIGS. 2A to 2C are graphs showing quantification results of target genes expressed in nasal mucus of normal group and Parkinson's patients.

FIG. 3A is a view showing the result of performing the ROC analysis on Parkin gene.

FIG. 3B is a view showing the result of performing the ROC analysis on the AIMP2 gene.

FIG. 4A is a view showing the relationship between Parkin-gene transcript levels and the H & Y stage.

FIG. 4B is a view showing the relationship between Parkin gene transcript levels and UPDRS rating.

FIG. 4C is a view showing the relationship between AIMP2 gene transcript levels and the H & Y stage.

FIG. 4D is a view showing the relationship between AIMP2 gene transcript levels and UPDRS rating.

FIG. 5 is a view showing the results of comparing AIMP2 and Parkin gene transcript levels in the normal group and MSA patients.

DETAILED DESCRIPTION

In the following detailed description, reference is made to the accompanying drawing, which forms a part hereof. The illustrative embodiments described in the detailed description, drawings, and claims are not meant to be limiting. Other embodiments may be utilized, and other changes may be made, without departing from the spirit or scope of the subject matter presented here.

Hereinafter, embodiments of the present disclosure are described in detail with reference to the accompanying drawings so that those skilled in the art may easily implement the present disclosure. However, the present disclosure may be embodied in many different forms and should not be construed as limited to the embodiments set forth herein. Further, portions unrelated to the description excluded to clearly explain the present disclosure.

Throughout the present specification, when a part "includes" a certain part, it means that one part may further include other parts without excluding other parts unless specifically described otherwise.

The term of indicating the extent "about" or "substantially" used in the present specification is intended to have meanings close to numerical values or ranges specified with an allowable error and intended to prevent accurate or absolute numerical values disclosed for understanding of the present disclosure from being illegally or unfairly used by any unconscionable third party. Further, the term "step of (~ing)" or "step of" used in the present specification does not mean "step for".

Throughout the present specification, the term "combination of" included in Markush type description means mixture or combination of one or more components, selected from a group consisting of components described in Markush type and thereby means that the present disclosure includes one or more components selected from the Markush group.

Throughout the present specification, the description of "A and/or B" means "A, B, or A and B."

Throughout the present specification, the term "diagnosis" means identifying the presence or characteristic of a pathological condition. Among them, the present disclosure is useful for the diagnosis of Parkinson's disease. The present disclosure includes predicting the onset and progression of Parkinson's disease. In particular, an early predictor of Parkinson's disease is very important, and according to the method of the present disclosure, Parkinson's disease-related genes or proteins in nasal mucus which can be easily collected from suspected patients with Parkinson's disease who have olfactory abnormalities may be used as a diagnostic marker for Parkinson's disease. Here, "marker for diagnosis or diagnosis marker" is a substance which can diagnose the disease by distinguishing the cells of Parkinson's disease patients from the cells of the normal people who does not have Parkinson's disease, and can be selected from organic biomolecules such as polypeptides, nucleic acids, lipids, glycolipids, glycoproteins, and sugars (monosaccharides, disaccharides, polysaccharides, etc.) which are increased or decreased in cells of Parkinson's disease patients compared to the cells of normal people.

Throughout the present specification, the term "nucleic acid" is meant to include any DNA or RNA, for example, chromosomes, mitochondria, viruses, and/or bacterial nucleic acids present in tissue samples. It includes one or both strands of a double-stranded nucleic acid molecule and includes any fragment or portion of an intact nucleic acid molecule.

Throughout the present specification, the term "gene" means any nucleic acid sequence or portion thereof that has a functional role in protein coding or transcription or in the regulation of other gene expression. The gene may consist of all nucleic acid encoding a functional protein or only a portion of a nucleic acid encoding or expressing a protein. Nucleic acid sequences may include gene abnormalities in exons, introns, initiation or termination regions, promoter sequences, other regulatory sequences, or unique sequences adjacent to genes.

Throughout the present specification, the term "gene expression" generally refers to a cellular process in which a transcript and further biologically active polypeptide is produced from a DNA sequence and exhibits biological activity in cells. In that sense, the gene expression includes not only transcriptional and translational processes, but also post-transcriptional and post-translational processes that may affect the biological activity of a gene or gene product. The processes include, but are not limited to, RNA synthesis, processing and transport, as well as post-translational modifications of polypeptide synthesis, transport and polypeptide. The present disclosure includes both mRNA expression and protein expression as an aspect of gene expression.

Throughout the present specification, the term "primer" means an oligonucleotide sequence which hybridizes to complementary RNA or DNA-target polynucleotides and functions as a starting point for the stepwise synthesis of polynucleotides from mononucleotides, for example, by the action of nucleotidyltransferases occurred in PCR.

Hereinafter, a composition for diagnosing Parkinson's disease, a kit for diagnosing Parkinson's disease, and a method for providing information for diagnosing Parkinson's disease are described in detail with reference to embodiments, examples, and drawings. However, the present disclosure is not limited to these embodiments, embodiments, and drawings.

A first aspect of the present disclosure relates to a composition for diagnosing Parkinson's disease, in which the composition includes an agent for measuring expression levels of Parkinson's disease-related genes in isolated nasal mucus.

The present disclosure's composition is to diagnose Parkinson's disease using nasal mucus, which is easily collectable compared with the cerebrospinal fluid commonly used to diagnose Parkinson's disease. Nasal mucus is collected from the nasal cavity in patients with Parkinson's disease, and by measuring the expression levels of Parkinson's disease-related genes from the nasal mucus, Parkinson's disease can be diagnosed early with high accuracy.

For example, the nasal mucus may be obtained from a nasal wash solution, but may not be limited thereto. For example, the nasal wash may be performed using saline or water (distilled water), but may not be limited thereto.

Measurement of expression levels of Parkinson's disease-related genes in the isolated nasal mucus may be to isolate the cells in the nasal mucus and to measure the expression levels of the gene in the cells, but may not be limited thereto.

According to an embodiment of the present disclosure, the Parkinson's disease-related gene may be selected from the group consisting of α-synuclein (SNCA), parkin, ZNF746 (PARIS), RNF146 c-Abl and AIMP2, but may not be limited thereto. The genes that are expressed differently in nasal mucus in Parkinson's patients compared to those in normal people can be used without limitation.

According to an embodiment of the present disclosure, the agent for measuring the expression level may include a nucleic acid primer that binds to a nucleic acid sequence of Parkinson's disease-related gene or its corresponding sequence or an antibody or aptamer that specifically binds to a peptide or protein expressed by the Parkinson's disease gene, but may not be limited thereto. Any method of quantifying gene expression levels, which is commonly performed in the technical field to which the present disclosure belongs may be used without limitation.

A second aspect of the present disclosure relates to a kit for diagnosing Parkinson's disease, in which the kit includes the composition according to the first aspect of the present disclosure.

When the kit of the present disclosure is applied to a PCR amplification process, the kit may optionally contain reagents necessary for PCR amplification, such as buffers, DNA polymerases (e.g., thermally stable DNA polymerases obtained from *Thermus aquaticus* (Taq), *Thermus thermophilus* (Tth), *Thermus filiformis, Thermis flavus, Thermococcus literalis* or *Pyrococcus furiosus* (Pfu)), DNA polymerase cofactors and dNTPs.

When the kit of the present disclosure is applied to an immunoassay, the kit may optionally include a secondary antibody and a substrate of the label. Furthermore, the kit according to the present disclosure may be manufactured in the multiple separate packaging or compartments containing the reagent components as described above.

A third aspect of the present disclosure relates to a method for providing information on diagnosing Parkinson's disease, in which the method includes separating nasal mucus from a suspected patient of Parkinson's disease, measuring expression level of a Parkinson's disease-related gene and its transcript, or a peptide or a protein expressed therefrom, from the cells in the nasal mucus and normalizing the measured results to expression of standard genes, and comparing the normalized expression level with the normalized expression level measured for normal subjects.

According to an embodiment of the present disclosure, the Parkinson's disease-related gene may be selected from the group consisting of α-synuclein (SNCA), parkin, ZNF746 (PARIS), RNF146, c-Abl and AIMP2, but may not be limited thereto.

According to an embodiment of the present disclosure, the standard gene may be a housekeeping gene, preferably GAPDH, β-actin, or tubulin. However, genes may be used without limitation as long as the genes exhibit constant expression among individuals regardless of the presence of Parkinson's disease.

According to an embodiment of the present disclosure, the expression level of the gene may be measured using reverse transcriptase polymerase (RT-PCR), competitive RT-PCR, real-time quantitative RT-PCR, quantitative RT-PCR, RNase protection method, Northern blotting or DNA chip technology and may be measured using sequencing qualitative, quantitative analysis or NGS, but may not be limited thereto.

According to an embodiment of the present disclosure, the expression level of the protein or peptide may be measured using Western blot, enzyme linked immunosorbent assay (ELISA), immunoprecipitation assay, complement fixation assay, fluorescence activated cell sorter (FACS) or a protein chip, but may not be limited thereto.

According to an embodiment of the present disclosure, the comparison of normalized expression levels may be carried out by comparing with a predetermined cutoff value, but may not be limited thereto. In this case, the cutoff value may be determined according to a ROC curve, which is a curve drawn with sensitivity and 1-specificity of the measured value. That is, after normalizing gene expression levels in nasal mucus of Parkinson's patients and nasal mucus of normal persons, the cutoff values are predetermined from the ROC curve results using the same. Then, the normalized value of the gene expression level in the nasal mucus of the individual to be diagnosed is compared with the predetermined cutoff value to provide information for the diagnosis of Parkinson's disease, but may not be limited thereto.

In the method for providing information on diagnosing Parkinson's disease according to the present disclosure, the measurement result of Parkinson's disease-related gene expression level (normalized expression level) may be compared with that of normal group or the predetermined cutoff value to diagnose Parkinson's disease.

According to an embodiment of the present disclosure, the presence of Parkinson's disease may be determined when the normalized expression level of Parkin is lower compared to the cutoff value.

According to an embodiment of the present disclosure, the presence of Parkinson's disease may be determined when the normalized expression level of AIMP2 is higher compared to the cutoff value.

The present disclosure relates to a new early diagnosis of Parkinson's disease. The present disclosure first suggests that Parkinson's disease can be diagnosed by analyzing transcripts from nasal mucus. Further, the present disclosure suggests that Parkinson's disease-related genes Parkin and AIMP2 may be efficiently utilized for Parkinson's disease-specific biomarkers.

Hereinafter, the present disclosure is described in more detail with reference to the following examples, but the following examples are for illustrative purposes only and are not intended to limit the scope of the present disclosure.

EXAMPLES

1. Subject Selection and Evaluation

In order to evaluate the expression of markers for Parkinson's disease and multiple system atrophy (MSA) in nasal mucus, 30 patients with Parkinson's disease, 10 patients with MSA, and 13 normal patients were selected. All patients were diagnosed with Parkinson's disease according to the United kingdom brain bank diagnostic criteria (UKBBDC), and MSA patients were diagnosed according to the criteria set forth in Gilman, S. et al. Second consensus statement on the diagnosis of multiple system atrophy, Neurology 71, 670-.676. The following table 1 shows information about the test subject.

TABLE 1

|  | Control | PD | MSA | p value |
|---|---|---|---|---|
| N | 13 | 30 | 10 | |
| Male:female | 7:6 | 15:15 | 7:3 | 0.544 |
| Age(years) | 64.7 ± 8.9 | 70.7 ± 9.4 | 67.9 ± 2.2 | 0.093 |
| H&Y | | 2.5 ± 0.2 | | |
| UPDRS | | 28.2 ± 3.0 | | |

2. Whole Transcript Purification and cDNA Synthesis in Nasal Mucus Cells

After the sterile normal saline solution was introduced into normal or patient nasal cavity twice (puff; total of 10 μl), nasal fluid was collected through suction collector. Thereafter, the nasal fluid was transferred to a laboratory bench, and crust and debris were removed with a cell strainer (100 μm, SPL, Pocheon, Gyeonggi-do, South Korea). Then, the nasal fluid was centrifuged at 6000 rpm for 5 minutes, and the cell pellet was resuspended in 1 ml of Trizol. The result was stored and used at –80° C.

Confirmation experiments were first conducted to determine whether detectable levels of transcripts could be purified from nasal mucus cells (FIG. 1A). QIAzol was used for cell pellets of human nasal washes to purify total RNAs. In order to completely isolate trace RNAs of nasal mucus, yeast tRNAs was added as a carrier for purification. After synthesizing the cDNA library from the isolated RNAs, PCR was performed using a pair of primers for GAPDH. The results confirm that the cDNA library-specific PCR product was synthesized on an agarose gel (FIG. 1B). Comparison results of the cDNA library synthesized from the purified RNA in the neuroblastoma cell line SH-SY5Y could demonstrate that there was only small amount of GAPDH transcript that was detectable by PCR.

3. Quantification of Target Gene by RTO PCR

The cDNA library was synthesized for nasal mucus in normal and Parkinson's patients, and then a pair of primers which is specific for Parkinson's disease-related genes (α-synuclein, c-Abl, RNF146, AIMP2, Parkin and ZNF746 (PARIS)) were designed to perform RTQ PCR. Information on the primers used is shown in Table 2 and Sequence Listing. The fluorescence of SYBR green was measured at each amplification step. Peaks were identified for the amplicons of the target gene in the melt curve stage to confirm the selectivity of the PCR products.

TABLE 2

| | Gene | Direction of Primer | Sequence |
|---|---|---|---|
| 1 | c-Abl | Forward | CATCACGCCAGTCAACAGTCT (SEQ ID NO: 1) |
| | | Reverse | GTACACCCTCCCTTCGTATCT (SEQ ID NO: 2) |
| 2 | α-synuclein | Forward | AAGAGGGTGTTCTCTATGTAGGC (SEQ ID NO: 3) |
| | | Reverse | GCTCCTCCAACATTTGTCACTT (SEQ ID NO: 4) |
| 3 | AIMP2 | Forward | AGGTAAAGCCCTATCACGGG (SEQ ID NO: 5) |
| | | Reverse | ACAGGTTAGACTCTTCCTGCA (SEQ ID NO: 6) |
| 4 | arkin | Forward | CAGCAGTATGGTGCAGCGGA (SEQ ID NO: 7) |
| | | Reverse | TCAAATACGGCACTGCACTC (SEQ ID NO: 8) |
| 5 | PARIS | Forward | GCTGGAATTTCCGGTGTAAACC (SEQ ID NO: 9) |
| | | Reverse | GGGGTCCAAGATGGCCTCT (SEQ ID NO: 10) |
| 6 | RNF146 | Forward | ATTCCCGAGGATTTCCTTGACA (SEQ ID NO: 11) |
| | | Reverse | GCTCATCGTACTGCCACCA (SEQ ID NO: 12) |
| 7 | OMP | Forward | TACCGCCTCAACTTCACCCA (SEQ ID NO: 13) |
| | | Reverse | CCTCCTTGCGCCAGAAGATG (SEQ ID NO: 14) |
| 8 | GAPDH | Forward | AAACCCATCACCATCTTCCAG (SEQ ID NO: 15) |
| | | Reverse | AGGGGCCATCCACAGTCTTCT (SEQ ID NO: 16) |

Because the amplicons of the PCR products for the nasal mucus cDNA library of the normal group and Parkinson's patients had one main peak for the target genes, it was confirmed that the PCR for the nasal mucus library was successfully performed.

The quantitative value of each genome in the nasal mucus of the normal group (CTRL) and Parkinson's patient (IPD) was normalized to the quantitative value of GAPDH used as internal loading control to identify the relative amounts of target genes in each group. FIG. 2A shows the relative transcript amounts of parkin and RNF146. FIG. 2B shows the relative transcript amounts of AIMP2 and PARIS. FIG. 2C shows the relative transcript amounts of c-Abl and α-synuclein. An unpaired two-tailed student t test was performed for significance (*P<0.05, P<0.01, *P<0.001, n.s=no significance). Quantitative value for each gene was normalized to the expression level of GAPDH and then calculated as relative values in each group. c-Abl, RNF146 and Parkin showed a significant quantitative decrease in the nasal mucus of Parkinson's patients, and α-synuclein, and AIMP2 showed an increase (FIGS. 2A to 2C). Surprisingly, RNF146, AIMP2 and Parkin had little variation between samples in the normal group (FIGS. 4B and 4C). In particular, AIMP2 and Parkin showed significance with a high level of confidence and exhibited a change in their amount in nasal mucus of Parkinson's patients.

Parkin and AIMP2 are known genes that are linked to Parkinson's disease pathology. Parkin is an E3 ligase enzyme that mediates ubiquitination labeling of substrate proteins and degradation by proteasomes. Mutations of this gene are known to cause the recessive inheritance of Parkinson's disease by inhibiting Parkin's enzymatic activity. It has also been reported that Parkin's mutations as well as reduction of nitrosylation, phosphorylation, and solubility are involved in sporadic Parkinson's disease pathology. There has been no previous report on the reduced association of Parkinson's disease with Parkin transcripts in nasal wash solution. AIMP2 is a toxic protein regulated by Parkin and is present at low levels in normal conditions. However, AIMP2 has been reported by Parkinson's midbrain tissue autopsy that quantitative accumulation occurs in the case of Parkin's mutation or enzyme activity decrease. In particular, animal experiments have shown that accumulation of AIMP2 plays an important pathology in causing major lesions in Parkinson's disease including the death of dopamine neurons. Similarly, there has been no reported on changes in AIMP2 transcripts and disease linkages in nasal wash solution in Parkinson's disease patients. Therefore, the present disclosure first confirmed that the decrease of Parkin transcripts and the increase of AIMP2 transcripts in nasal mucus could be used as early diagnostic markers as risk factors for the development of Parkinson's disease.

4. ROC Curve Analysis for Parkin and AIPM2

In particular, as shown in FIGS. 3A and 3B, the cutoff value of the normalized gene expression level calculated from the ROC curve was about 0.359 for Parkin (reversal value) and its sensitivity and specificity, respectively, were calculated to about 76.7% and about 76.9%. For AIMP2, its cutoff value, sensitivity and specificity, respectively, were calculated to about 1.753, about 84.2%, and about 84.6%. Therefore, quantification of Parkin and AIMP2 transcripts in nasal mucus using these cutoff values is expected to be an accurate and useful means for early diagnosis of Parkinson's disease.

5. Analysis of Parkin and AIMP2 Transcript Expression Levels and their Association with H&Y and UPDRS The expression level of Parkin or AIMP2 in nasal mucus was examined in 14 Parkinson patients in the H&Y 1-2.5 stage, 15 Parkinson patients in the H&Y 3-5 stage, and 13 normal patients. As a result, as shown in FIGS. 4A and 4C, it was confirmed that there is a strong association between the two factors.

Further, the association between the UPDRS score and the level of transcript expression of Parkin or AIMP2 was examined. As shown in FIG. 4B, the higher the UPDRS score of the Parkin gene was, the lower the transcript expression level was with association therebetween. Therefore, it was confirmed that Parkin can be used not only for the diagnosis of Parkinson's disease but also for the prognostic diagnosis as a marker reflecting the stage of disease progression.

6. Identification of Parkin and AIMP2 Transcript Expression Levels and their Association with MSA The expression levels of Parkin and AIMP2 transcripts were confirmed with samples of 10 MSA patients and samples of normal people.

The results are shown in FIG. 5.

As shown in FIG. 5, Parkin showed the same pattern as Parkinson's disease, but AIMP2 showed the opposite pattern. The results confirmed that there is a possibility of early diagnosis of MSA as well as distinction from Parkinson's disease using Parkinson's and AIPM2 transcript expression levels.

The above description of the present disclosure is for illustrative purposes, and it will be understood that a person of ordinary skill in the technical field to which the present disclosure belongs may readily transform into another specific form without changing the technical spirit or essential characteristics of the present disclosure. Therefore, it should be understood that the examples described above are exemplary in all respects and not limiting. For example, each component described as a single type may be implemented in a distributed manner, and similarly, components described as distributed may be implemented in a combined form.

It should be interpreted that the scope of the present disclosure is indicated by the following claims rather than the above description, and all changes or modifications derived from the meaning and scope of the claims and their equivalents are included in the scope of the present disclosure.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for diagnosing Parkinson's disease, the method comprising:

obtaining a nasal mucus sample from a patient;

measuring expression level of a transcript related to one or more Parkinson's disease-related genes, from cells in the nasal mucus sample and normalizing the measured expression level, wherein the Parkinson's disease-related genes are parkin and AIMP2, and the expression level is measured by using one or more oligonucleotide comprising the nucleotide sequence of at least one of SEQ ID No. 5, 6, 7 or 8; and determining whether said patient has Parkinson's disease, by comparing the normalized expression level with an expression level obtained from normal subjects.

2. The method of claim 1, wherein the measured expression level is normalized based on an expression level of a standard gene, the standard gene comprising at least one of GAPDH, β-actin, or tubulin.

3. The method of claim 1, wherein the expression level of the genes is measured using reverse transcriptase polymerase chain reaction (RT-PCR), competitive RT-PCR, real-time quantitative RT-PCR, quantitative RT-PCR, RNase protection method, Northern blotting or DNA chip technology.

4. The method of claim 1, wherein the comparing of the normalized expression levels is carried out by comparing the normalized expression level of transcript measured in the nasal mucus sample with a predetermined cutoff value.

5. The method of claim 4, wherein said patient is determined to have Parkinson's disease when the normalized expression level of parkin transcript measured in the nasal mucus sample is lower compared to the cutoff value.

6. The method of claim 4, wherein said patient is determined to have Parkinson's disease when the normalized expression level of AIMP2 transcript measured in the nasal mucus sample is higher compared to the cutoff value.

7. A method for diagnosing Parkinson's disease, the method comprising:

measuring an expression level of parkin gene and an expression level of AIMP2 gene in a nasal mucus sample of a patient, wherein the measuring of the expression levels comprises detecting a gene transcript, and the expression levels are measured by using one or more oligonucleotide comprising the nucleotide sequence of at least one of SEQ ID No. 5, 6, 7 or 8; and determining whether said patient has Parkinson's disease based on the measured expression level of parkin gene and the measured expression level of AIMP2 gene.

8. The method of claim 7, wherein the gene transcript comprises an RNA.

9. The method of claim 7, further comprising measuring an expression level of one or more standard gene in the nasal mucus sample, and using the expression level of the one or more standard gene with the measured expression level of parkin and AIMP2 genes to determine whether said patient has Parkinson's disease.

10. The method of claim 7, wherein the measuring of the gene expression level of the parkin gene comprises using one or more oligonucleotide comprising the nucleotide sequence of SEQ ID No. 7 or 8.

11. The method of claim 7, wherein the measuring of the gene expression level of the AIMP2 gene comprises using one or more oligonucleotide comprising the nucleotide sequence of SEQ ID No. 5 or 6.

12. The method of claim 7, wherein the determining of whether said patient has Parkinson's disease comprises normalizing the measured expression level of parkin gene based on an expression level of a standard gene.

* * * * *

SEQUENCE LISTING

<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: c-Abl F

<400> SEQUENCE: 1
catcacgcca gtcaacagtc t                                            21

<210> SEQ ID NO 2
<211> LENGTH: 21
<212> TYPE: DNA
<213> ORGANISM: Artificial Sequence
<220> FEATURE:
<223> OTHER INFORMATION: c-Abl R

```
<400> SEQUENCE: 2
gtacaccctc ccttcgtatc t                                              21

<210> SEQ ID NO 3
<211> LENGTH: 23
<212> TYPE: DNA
<213> ORGANISM: Artificial Sequence
<220> FEATURE:
<223> OTHER INFORMATION: a-synuclein F

<400> SEQUENCE: 3
aagagggtgt tctctatgta ggc                                            23

<210> SEQ ID NO 4
<211> LENGTH: 22
<212> TYPE: DNA
<213> ORGANISM: Artificial Sequence
<220> FEATURE:
<223> OTHER INFORMATION: a-synuclein R

<400> SEQUENCE: 4
gctcctccaa catttgtcac tt                                             22

<210> SEQ ID NO 5
<211> LENGTH: 20
<212> TYPE: DNA
<213> ORGANISM: Artificial Sequence
<220> FEATURE:
<223> OTHER INFORMATION: AIMP2 F

<400> SEQUENCE: 5
aggtaaagcc ctatcacggg                                                20

<210> SEQ ID NO 6
<211> LENGTH: 21
<212> TYPE: DNA
<213> ORGANISM: Artificial Sequence
<220> FEATURE:
<223> OTHER INFORMATION: AIMP2 R

<400> SEQUENCE: 6
acaggttaga ctcttcctgc a                                              21

<210> SEQ ID NO 7
<211> LENGTH: 20
<212> TYPE: DNA
<213> ORGANISM: Artificial Sequence
<220> FEATURE:
<223> OTHER INFORMATION: Parkin F

<400> SEQUENCE: 7
cagcagtatg gtgcagcgga                                                20

<210> SEQ ID NO 8
<211> LENGTH: 20
<212> TYPE: DNA
<213> ORGANISM: Artificial Sequence
<220> FEATURE:
<223> OTHER INFORMATION: Parkin R

<400> SEQUENCE: 8
tcaaatacgg cactgcactc                                                20

<210> SEQ ID NO 9
<211> LENGTH: 22
```

-continued

<212> TYPE: DNA
<213> ORGANISM: Artificial Sequence
<220> FEATURE:
<223> OTHER INFORMATION: PARIS F

<400> SEQUENCE: 9
gctggaattt ccggtgtaaa cc                                              22

<210> SEQ ID NO 10
<211> LENGTH: 19
<212> TYPE: DNA
<213> ORGANISM: Artificial Sequence
<220> FEATURE:
<223> OTHER INFORMATION: PARIS R

<400> SEQUENCE: 10
ggggtccaag atggcctct                                                  19

<210> SEQ ID NO 11
<211> LENGTH: 22
<212> TYPE: DNA
<213> ORGANISM: Artificial Sequence
<220> FEATURE:
<223> OTHER INFORMATION: RNF146 F

<400> SEQUENCE: 11
attcccgagg atttccttga ca                                              22

<210> SEQ ID NO 12
<211> LENGTH: 19
<212> TYPE: DNA
<213> ORGANISM: Artificial Sequence
<220> FEATURE:
<223> OTHER INFORMATION: RNF146 R

<400> SEQUENCE: 12
gctcatcgta ctgccacca                                                  19

<210> SEQ ID NO 13
<211> LENGTH: 20
<212> TYPE: DNA
<213> ORGANISM: Artificial Sequence
<220> FEATURE:
<223> OTHER INFORMATION: OMP F

<400> SEQUENCE: 13
taccgcctca acttcaccca                                                 20

<210> SEQ ID NO 14
<211> LENGTH: 20
<212> TYPE: DNA
<213> ORGANISM: Artificial Sequence
<220> FEATURE:
<223> OTHER INFORMATION: OMP R

<400> SEQUENCE: 14
cctccttgcg ccagaagatg                                                 20

<210> SEQ ID NO 15
<211> LENGTH: 21
<212> TYPE: DNA
<213> ORGANISM: Artificial Sequence
<220> FEATURE:
<223> OTHER INFORMATION: GAPDH F

<400> SEQUENCE: 15

```
aaacccatca ccatcttcca g                                                      21

<210> SEQ ID NO 16
<211> LENGTH: 21
<212> TYPE: DNA
<213> ORGANISM: Artificial Sequence
<220> FEATURE:
<223> OTHER INFORMATION: GAPDH R

<400> SEQUENCE: 16
aggggccatc cacagtcttc t                                                      21
```